United States Patent
Li

(10) Patent No.: US 8,193,348 B2
(45) Date of Patent: Jun. 5, 2012

(54) SYSTEM AND METHOD FOR RECOVERING CAPROLACTAM FROM REARRANGEMENT MIXTURES

(75) Inventor: Chien-Hsien Li, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 304 days.

(21) Appl. No.: 12/474,968

(22) Filed: May 29, 2009

(65) Prior Publication Data

US 2009/0312542 A1    Dec. 17, 2009

(30) Foreign Application Priority Data

Jun. 13, 2008 (TW) ................ 97122056 A

(51) Int. Cl.
*C07D 201/16* (2006.01)
(52) U.S. Cl. ...................................... 540/540
(58) Field of Classification Search ............... 540/540
See application file for complete search history.

(56) References Cited

FOREIGN PATENT DOCUMENTS

TW        408109 B    10/2000

*Primary Examiner* — Bruck Kifle

(74) *Attorney, Agent, or Firm* — Sughrue Mion, PLLC

(57) ABSTRACT

A system and a method for recovering caprolactam from a rearrangement mixture are provided. The system includes a neutralization unit; a buffering unit for receiving a crude lactam solution containing impurities content below a standard value and being fed from the neutralization unit; a temporary storage unit for receiving a crude lactam solution containing impurities above the standard value and being fed from the neutralization unit; a temporary extraction unit for performing batch extraction to separate out a first lactam solution; an extraction unit for performing continuous extraction to separate out a second lactam solution; and a recovery unit for allowing caprolactam to be recovered. In the present system and method, the crude lactam solution is selectively fed into the extraction unit for continuous extraction or to the temporary extraction unit for batch extraction, thereby maintaining continuity of operation, enhancing separation efficiency, and reducing both material consumption and purification loadings.

17 Claims, 3 Drawing Sheets

US 8,193,348 B2

SYSTEM AND METHOD FOR RECOVERING CAPROLACTAM FROM REARRANGEMENT MIXTURES

FIELD OF INVENTION

The present invention relates to systems and methods for recovering caprolactam from rearrangement mixtures, and more particularly, to a system and a method for recovering caprolactam from a rearrangement mixture of cyclohexanone oxime and sulfuric acid.

BACKGROUND OF THE INVENTION

Caprolactam (CPL) is an important raw material for synthesizing chemical products, such as nylon 6, nylon 6.6, etc, and plays a significant role in the modern organic chemical industry. Caprolactam is commercially produced by a liquid phase Beckman rearrangement of cyclohexanone oxime in the presence of fuming sulfuric acid. The mixture solution containing fuming sulfuric acid and caprolactam after the rearrangement reaction is neutralized with ammonium hydroxide to give ammonium sulfate. Ammonium sulfate and crude lactam containing impurities are separated. The crude lactam is extracted with organic solvents, and then it is further purified to recover caprolactam.

FIG. 5 is a schematic diagram illustrating a conventional system for recovering caprolactam from a rearrangement mixture of cyclohexanone oxime and sulfuric acid in common industrial preparations. First of all, the mixture solution containing fuming sulfuric acid and caprolactam obtained after the Beckman rearrangement reaction, and ammonium hydroxide are fed into a neutralization unit 600 via lines 60 and 61, respectively, to carry out neutralization. The crude lactam solution containing impurities is fed into a buffering unit 610 via a line 62, and then it is continuously fed into an extraction unit 630 via a line 63. The organic solvent placed in an organic solvent storage tank 620 is continuously fed into the extraction unit 630 via a line 64, so as to extract the crude lactam solution. The organic and inorganic phases are discharged as effluent from the extraction unit 630, while the lactam solution containing caprolactam is fed into a recovery unit 640 via a line 65 to undergo subsequent purification steps, and caprolactam is recovered.

Taiwanese Patent No. 408109 discloses a method for recovering caprolactam from a rearrangement mixture after neutralization. The rearrangement mixture containing an aqueous caprolactam solution and an aqueous ammonium sulfate solution is extracted with organic solvents in a mixer, and then it is separated into an organic phase and an aqueous phase in a separator. Afterwards, caprolactam is recovered from the organic phase. However, due to an excessive amount of impurities contained in the cyclohexanone oxime raw material or incomplete initial reactions of cyclohexanone oxime, a low grade crude lactam solution may be formed, thereby causing an inseparable third phase between the organic phase and the aqueous phase to be formed during subsequent extractions using organic solvents. In this case, a continuous extraction device can't be smoothly operated, and thus inorganic solution and impurities accompanying the lactam solution all overflow into the subsequent purification steps, resulting in drastically increasing purification loadings, decreasing separation efficiency and raw material consumption. Continuous operation process is further interrupted and even stopped.

Therefore, it is desired to provide a method for recovering caprolactam with high separation efficiency, low raw material consumption, low purification loadings and a continuous operation process.

SUMMARY OF THE INVENTION

This invention provides a system for recovering caprolactam from a rearrangement mixture with high separation efficiency, comprising a neutralization unit for neutralization of rearrangement mixtures with base to obtain a first crude lactam solution containing impurity above a standard value and a second crude lactam solution containing impurity under the standard value; a temporary storage unit for receiving the first crude lactam solution; a buffering unit for receiving the second crude lactam solution from the neutralization unit; a temporary extraction unit for allowing the first crude lactam solution to be in contact with a first organic solvent to perform batch extraction, so as to separate out the first lactam solution and a first impurity containing minor amount of organic solvent; an extraction unit for continuous extraction in which the second crude lactam solution is in contact with a second organic solvent, so as to separate out the second caprolactam solution and a second impurity containing minor amount of organic solvent; and a recovery unit for recovering a first lactam solution subjected to the batch extraction and a second lactam solution subjected to the continuous extraction, so as to recover lactam from the first and second lactam solutions.

This invention further provides a system for recovering caprolactam from a rearrangement mixture, comprising a neutralization unit for neutralizing base with rearrangement mixtures to obtain a first crude lactam solution containing impurity above a standard value and a second crude lactam solution containing impurity under the standard value; a temporary storage unit for receiving the first crude lactam solution; a buffering unit for receiving the second crude lactam solution from the neutralization unit; a temporary extraction unit for allowing the first crude lactam solution to be in contact with a first organic solvent to perform batch extraction, so as to separate out the first lactam solution and a first impurity containing minor amount of organic solvent; an extraction unit for continuous extraction in which a combination of the second crude lactam solution from the buffering unit and the first lactam solution from the temporary extraction unit are in contact with a second organic solvent, so as to separate out the second caprolactam solution and a second impurity containing minor amount of organic solvent; and a recovery unit for recovering a first caprolactam solution subjected to the batch extraction and a second lactam solution subjected to the continuous extraction, so as to recover caprolactam from the second lactam solution.

This invention further provides a method for recovering caprolactam from a rearrangement mixture, comprising (a) neutralizing base with the rearrangement mixture to obtain a first crude lactam solution containing impurity above a standard value and a second crude lactam solution containing impurity under the standard value, and separating the first and the second crude lactam solutions; (b) feeding the first crude lactam solution into a temporary storage unit, and feeding the second crude lactam solution into a buffering unit; (c1) feeding a first organic solvent and the first crude lactam solution from the storage unit in a temporary extraction unit, allowing the first crude lactam solution to be in contact with a first organic solvent to carry out batch extraction, so as to separate out a first lactam solution and a first impurity containing a minor amount of organic solvent; (c2) continuously feeding a second organic solvent and the second crude lactam solution from the buffering unit into an extraction unit, allowing the second crude lactam solution to be in contact with the second organic solvent to carry out continuous extraction, so as to separate out a second lactam solution and a second impurity containing a minor amount of organic solvent; and (d) recovering a first lactam solution subjected to batch extraction and the second lactam solution subjected to continuous extraction, so as to recover caprolactam from the first and the second caprolactam solutions.

This invention further provides a method for recovering caprolactam from a rearrangement mixture, comprising (a) neutralizing base with the rearrangement mixture to obtain a first crude lactam solution containing impurity above a standard value and a second crude lactam solution containing impurity under the standard value, and separating the first and the second crude lactam solutions; (b) feeding the first crude lactam solution into a temporary storage unit, and feeding the second crude lactam solution into a buffering unit; (c1) feeding a first organic solvent and the first crude lactam solution from the storage unit in a temporary extraction unit, allowing the first crude lactam solution to be in contact with a first organic solvent to carry out batch extraction, so as to separate out a first lactam solution and a first impurity containing a minor amount of organic solvent; (c2) continuously feeding a second organic solvent and a combination of the first lactam solution from the temporary buffering unit and the second crude lactam solution from the buffering unit into an extraction unit, allowing the first and the second lactam solutions to be in contact with the second organic solvent to carry out extraction, so as to separate out a second lactam solution and a second impurity containing a minor amount of organic solvent; and (d) recovering a first lactam solution subjected to batch extraction and the second lactam solution subjected to continuous extraction, so as to recover caprolactam from the first and the second caprolactam solutions.

In the system and the method of the present invention, according to the quality of crude lactam solutions formed after neutralization, the crude lactam solutions are respectively fed into the extraction unit for continuous extraction or the temporary extraction unit for batch extraction, so that a continuous process can be attained to increase separation efficiency, decrease raw material consumption and achieves a less loading on subsequent purification steps.

DETAILED DESCRIPTION OF THE PREFERRED EMBODIMENTS

Illustrative embodiments of a system and a method for recovering caprolactam from a rearrangement mixture of cyclohexanone oxime and sulfuric acid the present invention are described as follows with reference to FIGS. 1 to 4. It should be understood that the drawings are simplified schematic diagrams only showing the components relevant to the present invention, and the layout of components could be more complicated in practical implementation.

Figure 1:
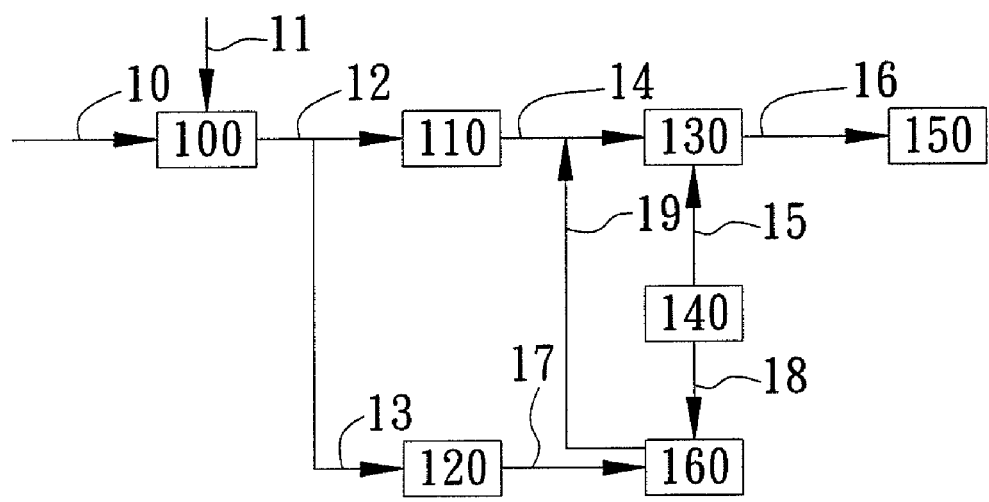
FIG. 1 is a schematic diagram illustrating the system for recovering caprolactam from a rearrangement mixture of cyclohexanone oxime and sulfuric acid according to the first embodiment of the present invention.

FIG. 1 is a schematic diagram illustrating the system for recovering caprolactam from a rearrangement mixture of cyclohexanone oxime and sulfuric acid according to the first embodiment of the present invention. As shown in FIG. 1, the rearrangement mixture of cyclohexanone oxime and sulfuric acid, and a base (such as, ammonium hydroxide) are fed into a neutralization unit 100 via lines 10 and 11, respectively, and neutralization is preformed to form a crude lactam solution. When the reactants have poor quality or the reaction is incomplete at initial stages, the content of organic impurities (e.g. ketones and alcohols) in the obtained crude lactam solution is higher than the standard value, for example, higher than 500 ppm, 200 ppm, or 150 ppm, and/or the extinction of the crude lactam solution is more than 2.3, 2, or 1.7. The first crude lactam solution containing impurities above the standard value is introduced into a temporary storage unit 120 via a line 13. On the contrary, when the content of organic impurities (e.g. ketones and alcohols) in the obtained crude lactam solution is under the standard value, for example, under 500 ppm, preferably under 200 ppm, and more preferably under 150 ppm, and/or the extinction of the crude lactam solution is less than 2.3, preferably less than 2, and more preferably less than 1.7, the second crude lactam solution containing impurities under the standard value is introduced into a buffering unit 110 via a line 12.

The second crude lactam solution containing impurities under the standard value is continuously fed into an extraction unit 130 via a line 14 after it is fed into the buffering unit 110.

On the other hand, the first crude lactam solution containing impurities above the standard value in the temporary storage unit 120 is fed into a temporary extraction unit 160 via a line 17, and then mixed with a first organic solvent introduced into the temporary extraction unit 160 via a line 18, undergoing one or more, usually one to three batch extractions. In this embodiment, it is preferable to perform batch extraction for three times. Normally, the first organic solvent and the first crude lactam solution are mixed in a ratio of 1:1 to 3:1 by volume, preferably 1.5:1 to 2.5:1 by volume, and more preferably 1.7:1 to 2.3:1 by volume. A first lactam solution containing 2 to 25 wt % of caprolactam, preferably 10 to 25 wt % of caprolactam, is separated from the temporary extraction unit 160 after batch extraction and standing. In this embodiment, the first lactam solution separated from the temporary extraction unit 160 is mixed with the second crude lactam solution via a line 19, and then it is fed into the extraction unit 130. Simultaneously, a second organic solvent stored in an organic solvent storage tank 140 is fed into the extraction unit 130 via a line 15 to be in contact with the second crude lactam solution and the first lactam solution for undergoing continuous extraction and separating out a second lactam solution containing 15 to 30 wt % caprolactam, preferably 20 to 30 wt % caprolactam. Next, the second lactam solution is introduced into a recovery unit 150 via a line 16, and caprolactam is recovered by means of distillation, evaporation, etc.

Organic solvents used in extraction include aromatic hydrocarbons, hydrocarbons substituted with halogen atoms, and linear or cyclic aliphatic alcohols with 4 to 10 carbon atoms. The first and the second organic solvents used in the present system can be the same or different, and examples thereof include, but not limited to, benzene, toluene, chloroform, etc. It is preferable to use the same organic solvent, e.g. benzene, as the first and the second organic solvents to perform extraction.

Figure 2:
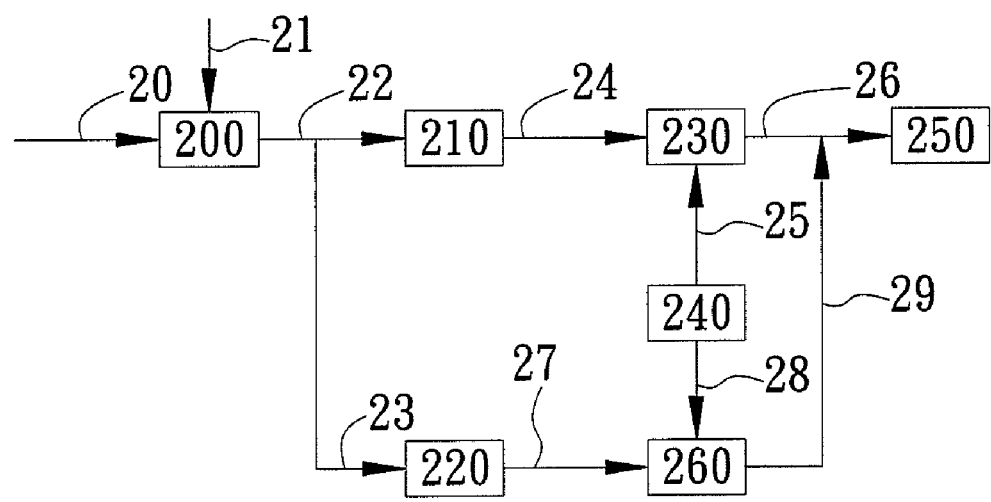
FIG. 2 is a schematic diagram illustrating the system for recovering caprolactam from a rearrangement mixture of cyclohexanone oxime and sulfuric acid according to the second embodiment of the present invention.

FIG. 2 is a schematic diagram illustrating the system for recovering caprolactam from a rearrangement mixture of cyclohexanone oxime and sulfuric acid according to the second embodiment of the present invention. As the first embodiment, the rearrangement mixture of cyclohexanone oxime and sulfuric acid, and a base are fed into a neutralization unit 200 via lines 20 and 21, respectively, and neutralization is performed to form a crude lactam solution. When the reactants have poor quality or the reaction is incomplete at initial stages, the content of organic impurities (e.g. ketones and alcohols) in the obtained crude lactam solution is higher than the standard value, for example, higher than 500 ppm, 200 ppm, or 150 ppm, and/or the extinction of the crude lactam solution is more than 2.3, 2, or 1.7. The first crude lactam solution containing impurities above the standard value is introduced into a temporary storage unit 220 via a line 23. On the contrary, when the content of organic impurities (e.g. ketones and alcohols) in the obtained crude lactam solution is under the standard value, for example, under 500 ppm, preferably under 200 ppm, and more preferably under 150 ppm, and/or the extinction of the crude lactam solution is less than 2.3, preferably less than 2, and more preferably less than 1.7, the second crude lactam solution containing impurities under the standard value is introduced into a buffering unit 210 via a line 22.

The second crude lactam solution containing impurities under the standard value is continuously fed into an extraction unit 230 via a line 24 after it is fed into buffering unit 210. Simultaneously, a second organic solvent stored in an organic solvent storage tank 240 is fed into the extraction unit 230 via a line 25 to be in contact with the second crude lactam solution to undergo continuous extraction and separating a second lactam solution containing 15 to 30 wt % caprolactam, preferably 20 to 30 wt % caprolactam. Next, the second lactam solution is introduced into a recovery unit 250 via line 26, and caprolactam is recovered by means of distillation, evaporation, etc.

On the other hand, the first crude lactam solution containing impurities above the standard value in the temporary storage unit 220 is fed into a temporary extraction unit 260 via a line 27, and then it is mixed with a first organic solvent introduced into the temporary extraction unit 260 via a line 28 to undergo one or more batch extractions. The first organic solvent and the first crude lactam solution are mixed in a ratio of 1:1 to 3:1 by volume, preferably 1.5:1 to 2.5:1 by volume, and more preferably 1.7:1 to 2.3:1 by volume. A first lactam solution is separated from the temporary extraction unit 260 after batch extraction and standing. In this embodiment, the first lactam solution separated from the temporary extraction unit 260 is mixed via a line 29 with the second lactam solution separated from the extraction unit 230 in a ratio of 0.005:1 to 0.1:1 by volume, and preferably 0.01:1 to 0.05:1 by volume, and then it is fed into the recovery unit 250 to recover caprolactam.

Figure 3:
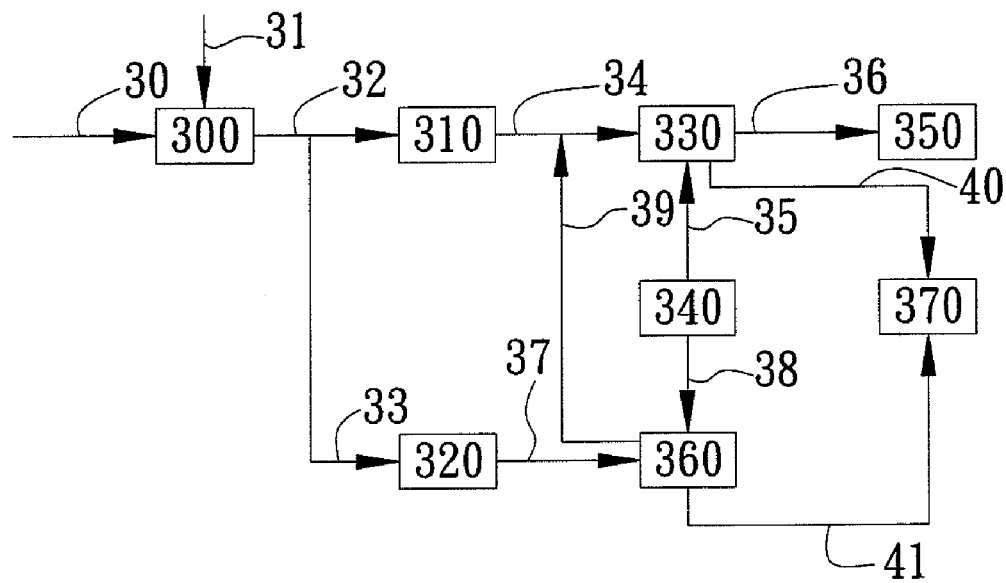
FIG. 3 is a schematic diagram illustrating the system for recovering caprolactam from a rearrangement mixture of cyclohexanone oxime and sulfuric acid according to the third embodiment of the present invention.

FIG. 3 is a schematic diagram illustrating the system for recovering caprolactam from a rearrangement mixture of cyclohexanone oxime and sulfuric acid according to the third embodiment of the present invention. As shown in FIG. 3, the rearrangement mixture of cyclohexanone oxime and sulfuric acid, and a base are fed into a neutralization unit 300 via lines 30 and 31, respectively, and neutralization is performed to form a crude lactam solution. When the reactants have poor quality or the reaction is incomplete at initial stages, the content of organic impurities (e.g. ketones and alcohols) in the obtained crude lactam solution is higher than the standard value, for example, higher than 500 ppm, and/or the extinction of the crude lactam solution is more than 2.3, the first crude lactam solution containing impurities above the standard value is introduced into a temporary storage unit 320 via a line 33. On the contrary, when the content of organic impurities (e.g. ketones and alcohols) in the obtained crude lactam solution is under the standard value, for example, under 500 ppm, and/or the extinction of the crude lactam solution is less than 2.3, the second crude lactam solution containing impurities under the standard value is introduced into a buffering unit 310 via a line 32.

The second crude lactam solution containing impurities under the standard value is continuously fed into an extraction unit 330 via a line 34 after it is fed into the buffering unit 310.

On the other hand, the first crude lactam solution containing impurities above the standard value in the temporary storage unit 320 is fed into a temporary extraction unit 360 via a line 37, and then it is mixed with a first organic solvent introduced into the temporary extraction unit 360 via a line 38 to undergo one to three batch extractions. A first lactam solution containing 2 to 25 wt % caprolactam, preferably 10 to 25 wt % caprolactam, is separated out from the temporary extraction unit 360 after batch extraction and standing. The first lactam solution is mixed with the second crude lactam solution via a line 39, and then it is fed into the extraction unit 330. Simultaneously, a second organic solvent stored in an organic solvent storage tank 340 is fed into the extraction unit 330 via a line 35 to be in contact with the second crude lactam solution and the first lactam solution to undergo continuous extraction and separating out a second lactam solution. Next, the second lactam solution is introduced into a recovery unit 350 via a line 36, and caprolactam is recovered by means of distillation, evaporation, etc.

In this embodiment, a second lactam solution containing 15 to 30 wt % caprolactam, and preferably 20 to 30 wt % caprolactam is separated out from the extraction unit 330 after the second crude lactam solution and the first lactam solution are continuously extracted with a second organic solvent. The second lactam solution is fed into the recovery unit 350 via the line 36, and second impurity containing a minor amount of organic solvents, which is separated out from extraction unit 330, is introduced into a steam stripping unit 370 via a line 40 to recover the organic solvents. Simultaneously, a first lactam solution and first impurity containing a minor amount of organic solvents are separated from the temporary extraction unit 360 after the first crude lactam solution is extracted with the first organic solvent and stands. The first lactam solution is mixed with the second crude lactam solution via the line 39, and the first impurity containing a minor amount of organic solvents is introduced into the steam stripping unit 370 via line 41 to recover the organic solvent.

Figure 4:
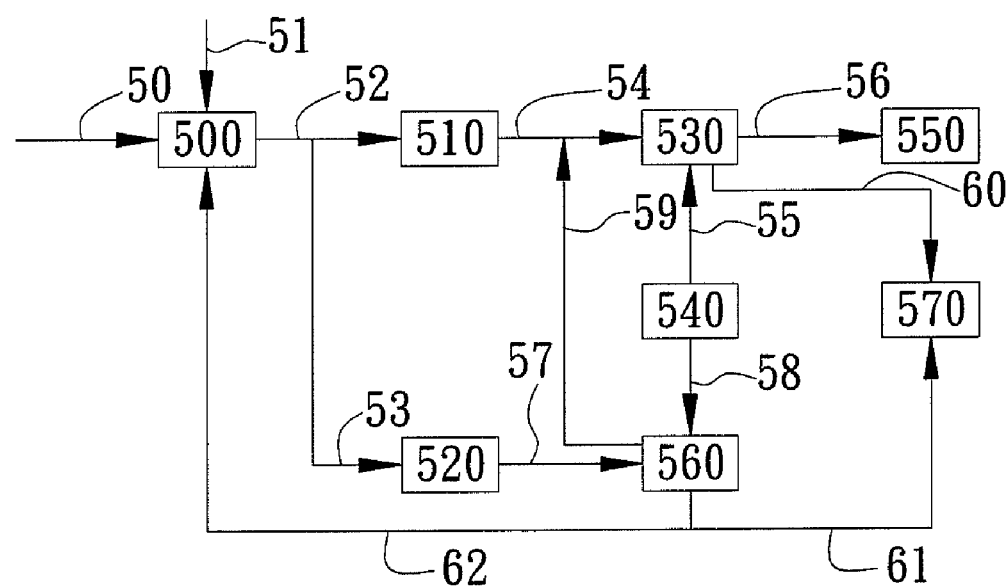
FIG. 4 is a schematic diagram illustrating the system for recovering caprolactam from a rearrangement mixture of cyclohexanone oxime and sulfuric acid according to the fourth embodiment of the present invention.
Figure 5:
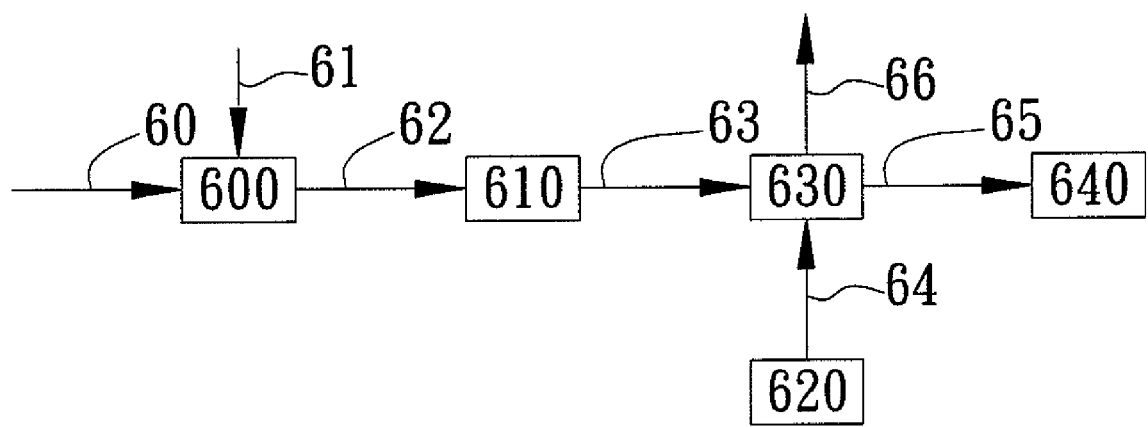
FIG. 5 is a schematic diagram illustrating a conventional system for recovering caprolactam from a rearrangement mixture of cyclohexanone oxime and sulfuric acid.

FIG. 4 is a schematic diagram illustrating the system for recovering caprolactam from a rearrangement mixture of cyclohexanone oxime and sulfuric acid according to the fourth embodiment of the present invention. As shown in FIG. 4, the rearrangement mixture of cyclohexanone oxime and sulfuric acid, and a base are fed into a neutralization unit 500 via lines 50 and 51, respectively, and neutralization is performed to form a crude lactam solution. When the reactants have poor quality or the reaction is incomplete at initial stages, the content of organic impurities (e.g. ketones and alcohols) in the obtained crude lactam solution is higher than the standard value, for example, higher than 500 ppm, and/or the extinction of the crude lactam solution is greater than 2.3. The first crude lactam solution containing impurities above the standard value is introduced into a temporary storage unit 520 via a line 53. On the contrary, when the content of organic impurities (e.g. ketones and alcohols) in the obtained crude lactam solution is under the standard value, for example, under 500 ppm, and/or the extinction of the crude lactam solution is less than 2.3, the second crude lactam solution containing impurities under the standard value is introduced into a buffering unit 510 via a line 52.

The second crude lactam solution containing impurities under the standard value is continuously fed into an extraction unit 530 via a line 54 after it is fed into the buffering unit 510.

On the other hand, the first crude lactam solution containing impurities above the standard value in the temporary storage unit 520 is fed into a temporary extraction unit 560 via a line 57, and then it is mixed with a first organic solvent introduced to the temporary extraction unit 560 via a line 58 to undergo one or more batch extractions. A first lactam solution is separated from the temporary extraction unit 560 after batch extraction and standing. The first lactam solution is mixed with the second crude lactam solution via a line 59, and then it is fed into the extraction unit 530. Simultaneously, a second organic solvent stored in an organic solvent storage tank 540 is fed into the extraction unit 530 via a line 55 to be in contact with the second crude lactam solution and the first lactam solution to undergo continuous extraction and separating out a second lactam solution. Next, the second lactam solution is introduced into a recovery unit 550 via a line 56 and caprolactam is recovered by means of distillation, evaporation, etc.

In this embodiment, a second lactam solution containing 15 to 30 wt % caprolactam, and preferably 20 to 30 wt % caprolactam, is separated out from the extraction unit 530 after the second crude lactam solution and the first lactam solution are continuously extracted with a second organic solvent. The second lactam solution is fed into the recovery unit 550 via the line 56, and second impurity containing a minor amount of organic solvents, which is separated out from the extraction unit 530, is introduced into a steam stripping unit 570 via a line 60 to recover the organic solvents. A first lactam solution containing 2 to 25 wt % caprolactam, preferably 10 to 25 wt % caprolactam, first impurity containing a minor amount of organic solvents, and a mixture containing sulfates and a minor amount of lactam are separated from the temporary extraction unit 560 after the first crude lactam solution is extracted with the first organic solvent and standing. The first lactam solution is mixed with the second crude lactam solution via a line 59, while the first impurity containing a minor amount of organic solvents is introduced into the steam stripping unit 570 via a line 61 to recover the organic solvents, and the mixture containing sulfates and a minor amount of lactam is further fed into the neutralization unit 500 via a line 62 to perform neutralization again.

The method for recovering caprolactam from a rearrangement mixture of cyclohexanone oxime and sulfuric acid according to the present invention is to first add a base, e.g. ammonium hydroxide, into the rearrangement mixture to undergo neutralization and then separating out a crude lactam solution. Then, a second crude lactam solution containing impurities under the standard value, for example, the content of organic impurities in this solution is under 500 ppm, 200 ppm, or 150 ppm; and/or its extinction is less than 2.3, less than 2, or less than 1.7, is introduced into a buffering unit. Conversely, a first crude lactam solution containing impurities higher than the standard value, for example, the content of organic impurities in the this solution is higher than 500 ppm, 200 ppm, or 150 ppm, and/or the extinction of the solution is more than 2.3, more than 2, or more than 1.7, is introduced into a temporary storage unit.

The second crude lactam solution in the buffering unit is continuously fed into an extraction unit via a line, and is in contact with a second organic solvent to perform continuous extraction, thereby separating out a second lactam solution containing 15 to 30 wt % caprolactam, preferably 20 to 30 wt %. Organic solvents used in extraction include aromatic hydrocarbons, hydrocarbons substituted with halogen atoms, and linear or cyclic aliphatic alcohols with 4 to 10 carbon atoms, and examples thereof include, but not limited to, benzene, toluene, chloroform, etc. It is preferable to carry out an extraction process with benzene.

The first crude lactam solution in the temporary storage unit is fed into a temporary extraction unit, and is in contact with a first organic solvent to perform extraction, thereby separating out a first lactam solution. The first organic solvent and the second organic solvent can be the same or different. In one preferable embodiment, the first organic solvent and the first crude lactam solution are mixed in a ratio of 1:1 to 3:1 by volume, preferably 1.5:1 to 2.5:1 by volume, and more preferably 1.7:1 to 2.3:1 by volume. Normally, one or more, usually one to three, batch extractions are performed. Then, a first lactam solution containing 2 to 25 wt % caprolactam, preferably 10 to 25 wt % caprolactam, is separated out after batch extraction and standing.

The first lactam solution separated from the temporary extraction unit can be mixed with the second lactam solution separated from the extraction unit, for example, in a ratio of 0.005:1 to 0.1:1 by volume, preferably 0.01:1 to 0.05:1 by volume, and then subsequent purification steps are performed to recover caprolactam. Optionally, the first lactam solution separated from the temporary extraction unit may be mixed firstly with the second crude lactam solution, and then is fed into an extraction unit to undergo continuous extraction. Next, purification process is performed to recover caprolactam.

Furthermore, a steam stripping device can be applied to the present method. A first and a second impurity containing organic solvents, being separated out from a temporary extraction device and an extraction device, respectively, are stripped by steam to recover organic solvents. These recovered solvents can be re-used. On the other hand, after the first crude lactam solution is batch extracted with the first organic solvent one or more times and stands and if a mixture containing sulfates and a minor amount of lactam is further separated out other than a first lactam solution and a first impurity containing organic solvents, the mixture can be fed into the neutralization device via a line to neutralize rearrangement mixtures with bases.

In the present system and method for recovering caprolactam from a rearrangement mixture, depending on the quality of a crude lactam solution formed after neutralization, the crude lactam solution is either fed into a buffering unit and to undergo subsequent continuous extractions or a temporary storage unit to undergo subsequent batch extraction. Consequently, contaminated, low-grade crude lactam is not fed into an extraction device, but is instead fed into a mixing-separation unit to undergo batch extraction or another continuous extraction. Hence, continuity of operation can be maintained, separation efficiency can be enhanced, and material consumption and purification loadings can both be reduced.

The invention has been described using exemplary preferred embodiments. However, it is to be understood that the scope of the invention is not limited to the disclosed arrangements. The scope of the claims, therefore, should be accorded the broadest interpretation, so as to encompass all such modifications and similar arrangements.

What is claimed is:

1. A method for recovering caprolactam from a rearrangement mixture of cyclohexanone oxime and sulfuric acid, comprising the steps of:
    (a) neutralizing the rearrangement mixture with a base in a neutralization device to obtain a first crude lactam solution containing impurities above a standard value and a second crude lactam solution containing impurities below the standard value;
    (b) feeding the first crude lactam solution into a temporary storage device, and feeding the second crude lactam solution into a buffering device;
    (c1) feeding a first organic solvent and the first crude lactam solution in the temporary storage device into a temporary extraction device, allowing the first crude lactam solution to be in contact with the first organic solvent to perform batch extraction, so as to obtain a first lactam solution and a first impurity containing a minor amount of organic solvents;
    (c2) feeding a second organic solvent and one of the second crude lactam solution in the buffering device and a combination of the second crude lactam solution and the first lactam solution continuously into an extraction device to perform continuous extraction, so as to obtain a second lactam solution and a second impurity containing a minor amount of organic solvents; and
    (d) recovering caprolactam from the second lactam solution after the continuous extraction.

2. The method according to claim 1, wherein the step (d) further comprises a step of:
    recovering caprolactam from the first lactam solution after the batch extraction, if the second organic solvent and the second crude lactam solution in the buffering device are continuously fed into the extraction device to perform the continuous extraction.

3. The method according to claim 2, wherein the first lactam solution is mixed with the second lactam solution in a ratio of 0.005:1 to 0.1:1 by volume, and the caprolactam is recovered.

4. The method according to claim 1, wherein the base is ammonium hydroxide.

5. The method according to claim 1, wherein the second crude lactam solution contains impurities below 500 ppm.

6. The method according to claim 1, wherein the second crude lactam solution contains impurities below 200 ppm.

7. The method according to claim 1, wherein the batch extraction is repeated one to three times.

8. The method according to claim 1, wherein the first organic solvent and the first crude lactam solution are mixed in a ratio of 1:1 to 3:1 by volume.

9. The method according to claim 1, wherein the first organic solvent and the second organic solvent are independently selected from the group consisting of aromatic hydrocarbons, hydrocarbons substituted with halogen atoms, and linear or cyclic aliphatic alcohols with 4 to 10 carbon atoms.

10. The method according to claim 1, wherein the first organic solvent and the second organic solvent are the same.

11. The method according to claim 1, wherein the first organic solvent and the second organic solvent are both benzene.

12. The method according to claim 1, wherein the second lactam solution contains 15 to 30 wt % caprolactam.

13. The method according to claim 1, wherein the first lactam solution contains 2 to 25 wt % caprolactam.

14. The method according to claim 1, further comprising a step of stripping by steaming the first impurity fed from the temporary extraction device and the second impurity fed from the extraction device.

15. The method according to claim 1, wherein after the first crude lactam solution is extracted with the first organic solvent, the first crude lactam solution stands to separate out a mixture containing sulfates and a minor amount of lactam.

16. The method according to claim 15, wherein the mixture is fed into the neutralization device again to repeat the neutralization of step (a).

17. The method according to claim 1, wherein step (a) further comprises a step of detecting the amounts of the impurities of the first and second crude lactam solutions.

* * * * *